United States Patent
Clark

(10) Patent No.: US 11,053,187 B2
(45) Date of Patent: Jul. 6, 2021

(54) PROCESS FOR CARBONYLATING DIMETHYL ETHER

(71) Applicant: Ineos Acetyls UK Limited, Lyndhurst (GB)

(72) Inventor: Thomas Edward Clark, Middlesex (GB)

(73) Assignee: Ineos Acetyls UK Limited, Lyndhurst (GB)

( * ) Notice: Subject to any disclaimer, the term of this patent is extended or adjusted under 35 U.S.C. 154(b) by 0 days.

(21) Appl. No.: 16/604,297

(22) PCT Filed: Apr. 10, 2018

(86) PCT No.: PCT/EP2018/059136
§ 371 (c)(1),
(2) Date: Oct. 10, 2019

(87) PCT Pub. No.: WO2018/189162
PCT Pub. Date: Oct. 18, 2018

(65) Prior Publication Data
US 2020/0031755 A1     Jan. 30, 2020

(30) Foreign Application Priority Data

Apr. 12, 2017 (GB) ..................... 1705882

(51) Int. Cl.
*C07C 67/37* (2006.01)
*C07C 69/14* (2006.01)
*B01J 29/18* (2006.01)
*B01J 38/52* (2006.01)

(52) U.S. Cl.
CPC .............. *C07C 67/37* (2013.01); *B01J 29/18* (2013.01); *B01J 38/52* (2013.01); *C07C 69/14* (2013.01)

(58) Field of Classification Search
CPC .......... C07C 67/37; C07C 69/14; B01J 29/18; B01J 38/52
See application file for complete search history.

(56) References Cited

U.S. PATENT DOCUMENTS 4,792,620 A * 12/1988 Paulik ................. B01J 31/0231
560/232

FOREIGN PATENT DOCUMENTS

| EP | 0596632 A1 | 5/1994 | | |
|---|---|---|---|---|
| EP | 1985608 A1 | 10/2008 | | |
| WO | 200107393 A1 | 2/2001 | | |
| WO | 2005105720 A1 | 11/2005 | | |
| WO | 2006121778 A1 | 11/2006 | | |
| WO | WO 2010/061169 A1 | 6/2010 | | |
| WO | WO 2014/111508 A1 | 7/2014 | | |
| WO | WO-2014111508 A1 * | 7/2014 | ............. | C07C 67/37 |
| WO | WO 2014/135660 A1 | 9/2014 | | |
| WO | WO 2014/135662 A2 | 9/2014 | | |
| WO | WO 2017/182359 A1 | 10/2017 | | |
| WO | WO 2010/130973 A2 | 11/2018 | | |

OTHER PUBLICATIONS

Norskov et al, Nature Chemistry, Towards the Computational Design of Solid Catalysts, 2009, 1, pp. 37-46. (Year: 2009).*

Liu et al, ACS Applied Materials & Interfaces, Facilely Synthesized H-Mordenite Nanosheet Assembly for Carbonylation of Dimethyl Ether, 2015, 7, pp. 8398-8403. (Year: 2015).*

* cited by examiner

*Primary Examiner* — Paul A Zucker

(74) *Attorney, Agent, or Firm* — McDonnell Boehnen Hulbert & Berghoff LLP

(57) ABSTRACT

A process for the production of methyl acetate by carbonylating dimethyl ether with carbon monoxide at a temperature of 250 to 350° C. in the presence of a zeolite catalyst and hydrogen such that the molar ratio of hydrogen to carbon monoxide is at least 1, and one or more compounds containing a hydroxyl functional group and in the absence of any added methyl acetate.

20 Claims, No Drawings

PROCESS FOR CARBONYLATING DIMETHYL ETHER

This invention relates in general to processes for carbonylating dimethyl ether with carbon monoxide in the presence of a zeolite catalyst to produce methyl acetate reaction product and, in particular to such carbonylation processes carried out under hydrogen-rich conditions, in the absence of any added methyl acetate and utilising one or more compounds containing a hydroxyl functional group.

Carbonylation processes such as the carbonylation of methanol conducted in the liquid phase in the presence of homogeneous Group VIII metal catalysts to produce acetic acid are operated commercially. Also known are gas phase carbonylation processes employing methanol and/or dimethyl ether using Group VIII metal or zeolite heterogeneous catalysts. Such processes are described in, for example EP-A-0 596 632, WO 01/07393, WO 2005/105720, WO 2006/121778 and WO 2010/061169.

EP-A-0 596 632 describes a vapour phase process for the carbonylation of methanol to produce acetic acid at high temperatures and pressures in the presence of a mordenite catalyst which has been loaded with copper, nickel, iridium, rhodium or cobalt.

WO 01/07393 describes a process for the catalytic conversion of a feedstock comprising carbon monoxide and hydrogen to produce at least one of an alcohol, ether and mixtures thereof and reacting carbon monoxide with the at least one of an alcohol, ether and mixtures thereof in the presence of a catalyst selected from solid super acids, heteropolyacids, clays, zeolites and molecular sieves, in the absence of a halide promoter, under conditions of temperature and pressure sufficient to produce at least one of an ester, acid, acid anhydride and mixtures thereof.

WO 2005/105720 describes a process for production of a carboxylic acid and/or an ester or anhydride thereof by carbonylating an aliphatic alcohol or reactive derivative thereof with carbon monoxide in the substantial absence of halogens at a temperature in the range 250 to 600° C. and a pressure in the range 10 to 200 bar in the presence of a mordenite catalyst which has been modified with copper, nickel, iridium, rhodium or cobalt and has as framework elements, silicon, aluminium, and at least one of gallium, boron and iron.

WO 2006/121778 describes a process for the production of a lower alkyl ester of a lower aliphatic carboxylic acid by carbonylating under substantially anhydrous conditions, a lower alkyl ether such as dimethyl ether, with carbon monoxide in the presence of a mordenite or ferrierite catalyst.

However, it is has been found that in zeolite catalysed carbonylation reactions of dimethyl ether, selectivity to methyl acetate product is generally lower than desirable due to the formation of by-products, and, in particular to the formation of the by-products, methane and $C_{2+}$ hydrocarbons. This problem is addressed in WO 2010/061169.

WO 2010/061169 exemplifies carbonylation reactions of dimethyl ether carried out under carbon monoxide-rich conditions in the presence of copper mordenite (non-templated) catalysts. Methane and $C_{2+}$ hydrocarbon by-product formation is shown in WO 2010/061169 to be reduced by employing methyl acetate as a feed component to the reaction.

WO 2014/135660 describes the use of zeolite catalysts which have been calcined at low temperature in processes for the carbonylation of dimethyl ether which processes are carried out utilising a molar ratio of hydrogen to carbon monoxide of at least 1.

WO 2014/135662 describes the use of zeolite catalysts which have been prepared using an organic structure directing agent in processes for the carbonylation of dimethyl ether which are carried out utilising a molar ratio of hydrogen to carbon monoxide of at least 1.

Applicant has found that carbonylation reactions of dimethyl ether with carbon monoxide which are conducted under high levels of hydrogen in the presence of zeolite catalysts, and in particular in the presence of templated zeolite catalysts, can lead to an undesirable increase in the deactivation rate of the zeolite catalyst, thereby reducing its lifetime.

Thus, there remains a need for a process for producing methyl acetate by reacting dimethyl ether with carbon monoxide in the presence of a zeolite catalyst and equimolar amounts or greater of hydrogen relative to carbon monoxide in which process the deactivation rate of the catalyst is at least maintained, and preferably is reduced. In particular there remains a need for a process for the production of methyl acetate by reacting dimethyl ether with carbon monoxide in the presence of a templated zeolite catalyst and equimolar amounts or greater of hydrogen relative to carbon monoxide, in which process the rate of catalyst deactivation is at least maintained, and preferably is reduced.

Accordingly, the present invention provides a process for the production of methyl acetate by carbonylation of dimethyl ether which process comprises contacting in a reactor dimethyl ether with carbon monoxide in the presence of a zeolite catalyst and hydrogen at a temperature of from 250 to 350° C. and at a molar ratio of hydrogen to carbon monoxide of at least 1, and wherein the process further comprises introducing into the reactor at least one compound containing a hydroxyl functional group and the process is carried out in the absence of added methyl acetate.

Advantageously, the present invention allows the deactivation rate of the zeolite catalyst to be reduced or at least maintained thereby allowing increased catalyst lifetime.

Thus, the present invention further provides a method of maintaining or reducing the deactivation rate of a catalyst in a process for the production of methyl acetate by carbonylation of dimethyl ether which process comprises contacting in a reactor dimethyl ether with carbon monoxide in the presence of a zeolite catalyst and hydrogen at a temperature of from 250 to 350° C. and at a molar ratio of hydrogen to carbon monoxide of at least 1, and wherein the process further comprises introducing into the reactor at least one compound containing a hydroxyl functional group and the process is carried out in the absence of added methyl acetate.

The present invention yet further provides for the use of one or more compounds containing a hydroxyl functional group to maintain or reduce the deactivation rate of a zeolite catalyst in a process for the production of methyl acetate by carbonylation of dimethyl ether which process comprises contacting in a reactor dimethyl ether with carbon monoxide in the presence of a zeolite catalyst and hydrogen at a temperature of from 250 to 350° C. and at a molar ratio of hydrogen to carbon monoxide of at least 1, and wherein the process further comprises introducing into the reactor at least one compound containing a hydroxyl functional group and the process is carried out in the absence of added methyl acetate.

'The one or more compounds containing a hydroxyl functional group' may be referred to in this specification and claims as 'the hydroxyl compound' or 'the hydroxyl compound(s)' as is appropriate.

In the present invention, methyl acetate is produced by carbonylating dimethyl ether with carbon monoxide in the presence of a zeolite catalyst, at least equimolar amounts of hydrogen relative to carbon monoxide and hydroxyl compound(s). Whereas, methyl acetate is a product of the carbonylation reaction, in the present invention methyl acetate is not added to the process either as a component of the process feed or as a component of any recycle stream to the process.

In the present invention, the components dimethyl ether, carbon monoxide, hydrogen, and the hydroxyl compound(s) may be introduced into the reactor as one or more feed streams. Each feed stream may comprise a single component or may be a mixture of two or more components. Such feed streams may contain impurities, such as nitrogen, helium, argon, methane and/or carbon dioxide, provided that they do not interfere with the conversion of dimethyl ether to methyl acetate product.

The hydroxyl compound(s) for use in the present invention is a compound which contains a hydroxyl functional group. Suitably, the hydroxyl compound is a compound solely consisting of carbon, hydrogen and oxygen atoms or solely consisting of hydrogen and oxygen atoms. Suitably, the hydroxyl compound is selected from the group consisting of one or more of aliphatic alcohols, aliphatic carboxylic acids, water and mixtures thereof.

Examples of suitable aliphatic alcohols include $C_1$-$C_4$ aliphatic alcohols such as methanol, ethanol, the propanols and the butanols.

Examples of suitable aliphatic carboxylic acids include $C_1$-$C_4$ aliphatic carboxylic acids, such as acetic acid, propionic acid and butanoic acid.

In some or all embodiments of the present invention, the hydroxyl compound is selected from water, acetic acid, methanol and mixtures of two or more thereof.

The hydroxyl compound(s) may be introduced in a total amount of up to 1 mol % based on the total gaseous feed (including recycles) to the process.

In some or all embodiments of the present invention, the hydroxyl compound(s) is introduced in a total amount of from 0.01 to 0.5 mol % based on the total gaseous feed (including recycles) to the process.

In some or all embodiments of the present invention, the process is carried out at a molar ratio of hydrogen to carbon monoxide of 1.5 to 4:1 and the hydroxyl compound is introduced in a total amount of 0.10 to 0.20 mol % based on the total gaseous feed to the process.

In the present invention, carbon monoxide and hydrogen are utilised at a molar ratio of hydrogen to carbon monoxide of at least 1. For the avoidance of doubt, the phrase 'a molar ratio of hydrogen to carbon monoxide of at least 1' means that the molar ratio of hydrogen/carbon monoxide is at least 1.

In some or all embodiments of the present invention, the molar ratio of hydrogen to carbon monoxide is in the range 1 to 12:1, for example 1 to 8:1, such as 1.5 to 4:1.

In the present invention, mixtures of hydrogen and carbon monoxide, optionally together with carbon dioxide, may be used. Such mixtures are generally referred to in the art as synthesis gas. Synthesis gas and processes for its commercial production are well known to the skilled person in the art and include reforming or partial oxidation of hydrocarbons, such as methane.

In some or all embodiments of the present invention, synthesis gas may comprise carbon dioxide in an amount of up to 50 mol %, for example in an amount of from 0.5 to 12 mol %.

In some or all embodiments of the present invention, dimethyl ether is used in an amount of from 1.0 mol % to 20 mol %, for example 1.5 mol % to 15 mol % based on the total gaseous feed (including recycles) to the process.

Preferably, dimethyl ether for use in the process is substantially pure, that is at least 99% pure dimethyl ether.

The carbonylation process is carried out in the presence of a zeolite catalyst. Zeolites are crystalline aluminosilicates which have framework structures constructed from tetrahedra of $SiO_4$ and $AlO_4$ that share vertices. Each framework topology contains a regular array of pores, channels and/or pockets that vary in size, shape and dimensionality. These framework topologies or structure types of zeolites are assigned three-letter structure codes by the Structure Commission of the International Zeolite Association, under the authority of IUPAC. A description of zeolites, their structure, properties and methods of synthesis can be found in The *Atlas of Zeolite Framework Types* (C. Baerlocher, W. M. Meier, D. H. Olson, 5$^{th}$ Ed. Elsevier, Amsterdam, 2001) in conjunction with the web-based version (http://www.iza-structure.org/databases/).

In the present invention, the zeolite should be effective to catalyse the carbonylation of dimethyl ether with carbon monoxide to produce methyl acetate as a reaction product. Suitable zeolites include those which have at least one channel or pocket (hereinafter collectively referred to as channels) which is defined by an 8-member ring. Preferably, the 8-member ring channel is interconnected with at least one channel defined by a ring with 10 or 12 members. The window size of the zeolite channel systems should be such that the reactant dimethyl ether and carbon monoxide molecules can diffuse freely in and out of the zeolite framework. Suitably, the window size of an 8-member ring channel or pocket is at least 2.5×3.6 Angstroms.

In some or all embodiments of the present invention, the zeolite has a framework type selected from the group consisting of MOR, FER, OFF, CHA, GME, MFS, EON and ETR.

Examples of zeolites of framework type MOR include mordenite. Examples of zeolites of framework type FER include ferrierite and ZSM-35. Examples of zeolites of framework type OFF include offretite. Examples of zeolites of framework type CHA include chabazite. Examples of zeolites of framework type GME include gmelinite. Examples of zeolites of framework type MFS include ZSM-57. Examples of zeolites of framework type EON include ECR-1. Examples of zeolites of framework type ETR include ECR-34.

In some or all embodiments of the present invention, the zeolite has a framework type MOR and is mordenite.

In some or all embodiments of the present invention, a zeolite may be in a hydrogen form or in an ammonium form, preferably in the hydrogen form In addition to the framework elements silicon and aluminium, a zeolite may have additional elements in its framework, such as framework elements selected from at least one of gallium, boron and iron.

Applicant has found that in carbonylation reactions of dimethyl ether which are carried out under hydrogen-rich conditions and also employ zeolite catalysts which are templated zeolite catalysts, the templated catalysts may exhibit superior catalytic activity, but they tend to deactivate relatively quickly. Advantageously, in such carbonylation processes employing templated zeolite catalysts under hydrogen-rich conditions, Applicant has found that by utilising at least one hydroxyl compound in the absence of added methyl acetate, improved deactivation rates of the templated zeolite catalysts can be achieved.

By 'templated zeolite' is meant throughout this specification and in the claims, a zeolite prepared from a synthesis mixture which comprises one or more organic structure directing agents.

In some or all embodiments of the present invention, the catalyst is a templated zeolite catalyst, for example a templated mordenite catalyst or a templated ferrierite catalyst. In these embodiments, the templated zeolite may be in a hydrogen form or a metal loaded form, for example the templated zeolite catalyst may be a copper mordenite or a silver mordenite.

Templated zeolites, for example templated mordenites and templated ferrierites are available commercially. Alternatively, they may be synthesised using well known preparation techniques.

Suitably, templated zeolites may be prepared from a synthesis mixture comprising a source of silica, a source of alumina, a source of alkali or alkaline earth metal, water and at least one organic structure directing agent.

The selection of the organic structure directing agent is dependent upon the desired zeolite structure to be achieved. However, useful organic structure directing agents include basic nitrogen compounds, such as primary amines, secondary amines, tertiary amines, salts and bases of quaternary ammonium compounds and heterocyclic nitrogen compounds. These compounds may be aliphatic or aromatic.

In some or all embodiments of the present invention, a templated mordenite zeolite may be prepared from a synthesis mixture which comprises silica, for example fumed silica, a water soluble aluminate, for example sodium aluminate, an alkali metal hydroxide, for example sodium hydroxide, and an organic structure directing agent, for example a quaternary ammonium compound, such as an aliphatic quaternary ammonium compound, for example a tetralkylammonium compound, in particular a tetraethylammonium compound and more particularly a tetralkylammonium halide, for example tetraethylammonium bromide, water, and optionally a source of gallium oxide.

To maintain a predetermined composition in the templated zeolite, it will generally be preferable to employ starting materials of known purity and composition so that composition control is maintained.

The components of a synthesis mixture are brought together in defined proportions in water to compose a zeolite-forming aqueous synthesis mixture. The aqueous synthesis mixture may be hydrothermally treated (with or without pressure) for a time and at a temperature to promote crystallisation.

Suitably, the synthesis mixture is maintained until crystals of the zeolite are formed, for example for a period of from 6 to 500 hours at elevated temperature, for example at a temperature of 80° C. to 210° C. At lower temperatures, for example 80° C., the crystallisation time is longer. Hydrothermal conditions found to be particularly suitable are a temperature of 150° C. to 170° C. for a period of about 3 to 14 days with agitation, for example with stirring, rotation or tumbling.

Crystallisation of the synthesis mixture may be performed with or without pressure but is suitably performed under pressure, for example in a stirred or tumbled autoclave. The resulting crystalline zeolite is then separated from the liquid and recovered, for example by filtration, washing with water, suitably with deionised or distilled water and dried. The synthetic zeolite crystallises as a fine powder which exhibits an x-ray diffraction pattern characteristic of that particular type of zeolite.

The proportions of the components of the synthesis mixture can be adjusted to produce the desired templated zeolite. To synthesise a templated mordenite, the following molar ratios, expressed as oxide ratios, of synthesis mixture components may be employed:

$SiO_2/M_2O_3$ from 10 to 100, preferably 20 to 60
$H_2O/Al_2O_3$ from 500 to 3000
$OSDA/Al_2O_3$ from 1 to 15
$Na_2O/Al_2O_3$ from 1 to 15, for example 1 to 10 wherein M is a trivalent metal selected from one or more of Al, Ga, B and Fe; and OSDA is an organic structure directing agent.

As a result of the crystallisation process, an as-synthesised templated zeolite contains, within its pores, the organic structure directing agent used in the synthesis mixture. Suitably, the organic structure directing agent is removed or substantially removed from within the pores of the zeolite, prior to its use in the present invention. A variety of removal methods may be used, for example combustion or thermal treatment methods. Suitably, at least 50% of the organic structure directing agent is removed from the zeolite, and preferably essentially all the organic structure directing agent is removed.

A preferred method of removal is by a thermal treatment, such as calcination, which may be carried out, for example at temperatures ranging from about 300° C. to about 650° C. Calcination may take place in the presence of an inert atmosphere, such as nitrogen or an oxidising atmosphere such as oxygen or air for a period of time ranging from about 1 to about 9 hours or longer.

In some or all embodiments of the present invention, the zeolite may be used in an ammonium or hydrogen form. Thus, an as-synthesised zeolite may be treated to reduce its alkali and alkaline earth metal content by conventional ion exchange procedures with replacing cations. In general, ion exchange is conducted with an aqueous solution of replacing cations, such as an aqueous solution of ammonium ions at temperatures of from about 25° C. to about 100° C. for a suitable time interval, for example about 1 to 6 hours. The degree of the ion-exchange can be varied by changing one or more of the duration of contact, concentration of the replacing cation solution and the temperature.

Following contact with an aqueous salt solution of the desired replacing cation, the zeolite may be washed with water and dried to produce a dry zeolite having the replacing cations occupying the alkali/alkaline earth metal sites.

The ammonium form of a zeolite may readily be converted to its hydrogen form by calcination, for example at temperatures in the range 300° C. to 650° C. Calcination causes the ammonium ion to decompose leaving the structure in a hydrogen form.

In some or all embodiments of the present invention, the zeolite is in hydrogen form and, in particular is a templated zeolite in hydrogen form.

As-synthesised zeolites are fine crystalline powders. Since a powder has no significant mechanical strength, its practical applications are limited. Mechanical strength can be conferred on a zeolite, such as by forming the zeolite into shaped particles. Processes for forming zeolites into shaped particles are well-known in the art and may be accomplished by forming a gel or paste of a zeolite powder with the addition of a suitable binder, subsequently extruding the gel or paste into the desired shape and then dried. The resultant extrudate may also be calcined, for example at temperatures of at least 450° C.

In some or all embodiments of the present invention, the zeolite is composited with at least one binder material. In these embodiments, the binder material may be a refractory inorganic oxide, suitably selected from silicas, aluminas, alumina-silicates, magnesium silicates, magnesium aluminium silicates, titanias and zirconias. Particularly useful binder materials include aluminas, alumina-silicates and silicas.

The relative proportions of zeolite and the binder material in a composite may vary widely, for example a binder material may be present in an amount in the range of 10% to 90% by weight of the composite.

Zeolite powders also may be formed into particles without the use of a binder material.

Preferably, the zeolite catalyst is dried prior to its use in the carbonylation process. Drying of the catalyst may be carried out by any suitable means, for example by heating to a temperature of from 60° C. to 500° C.

In some or all embodiments of the present invention, a zeolite has a silica to alumina molar ratio of from 6 to 90, for example of from 20 to 60.

In some or all embodiments of the present invention, the carbonylation process is carried out as a gaseous phase process.

Some components of the carbonylation process, for example dimethyl ether and/or the hydroxyl compound(s) may be in the liquid phase. However and desirably, any liquid components are vaporised, for example in a pre-vapourisation zone, prior to their use in the carbonylation process.

In the present invention, carbonylation is carried out at temperatures of from 250° C. to 350° C. In some or all embodiments of the present invention, carbonylation is carried out at a temperature of from 275 to 325° C.

In some or all embodiments of the present invention, carbonylation is carried out at pressures of from 1 to 100 barg, for example at pressures of from 50 to 100 barg.

In some or all embodiments of the present invention, carbonylation is carried out at a temperature of from 275° C. to 325° C. and at a pressure of from 50 to 100 barg.

The carbonylation process may be carried out at a gas hourly space velocity (GHSV) in the range 500 to 40,000 $h^{-1}$, for example in the range 2000 to 10,000 $h^{-1}$.

In some or all embodiments of the present invention, carbonylation is carried out at a temperature of from 275° C. to 325° C., a pressure of from 50 to 100 barg and a GHSV in the range 2000 to 10,000 $h^{-1}$.

The carbonylation process may be carried out using one or more beds of catalysts, suitably selected from fixed bed, fluidised bed and moving beds of catalyst.

The carbonylation process may be operated as either a continuous or a batch process, preferably as a continuous process.

The reaction product of the carbonylation process comprises mainly methyl acetate. The reaction product may also comprise lesser amounts of other components, for example acetic acid, unconverted reactants such as dimethyl ether and carbon monoxide and inert gases.

Desirably, methyl acetate is recovered from the reaction product. In general, the reaction product is withdrawn from the process as a vapour stream which may be cooled and condensed to recover a methyl acetate-rich liquid stream. Typically, the methyl acetate-rich liquid stream comprises mainly methyl acetate but it may also comprise minor amounts of one or more of unreacted dimethyl ether, water and dissolved gases. Methyl acetate may be recovered from the methyl acetate-rich liquid stream, for example by distillation and the recovered methyl acetate sold as such or used as a feedstock in downstream chemical processes.

In some or all embodiments of the present invention, some or all of recovered methyl acetate is converted to acetic acid, for example by a hydrolysis process.

Suitable hydrolysis processes for conversion of methyl acetate to acetic acid include catalytic distillation processes. Typically, in such catalytic distillation processes, methyl acetate is hydrolysed with water in a fixed-bed reactor in the presence of an acidic catalyst, such as an acidic ion exchange resin or a zeolite catalyst, to produce a mixture comprising acetic acid and methanol from which acetic acid and methanol may be separated by distillation, in one or more distillation stages.

The invention is now illustrated with reference to the following non-limiting Examples.

EXAMPLE 1

This Example demonstrates carbonylation of dimethyl ether with carbon monoxide in the presence of a templated zeolite catalyst under hydrogen-rich conditions and the addition of acetic acid, methanol or water.

Carbonylation was carried out in a stainless steel pipe reactor (1215 mm in length and 20.4 mm internal diameter) housing a catalyst bed of a uniform mixture of 110.0 mL 3.2 mm diameter templated mordenite catalyst extrudates and 203.2 mL of 3 mm diameter inert alumina spheres. Located within the catalyst bed were 9 points of a multipoint thermocouple. The effluent stream from the reactor was depressurized to atmospheric pressure and periodically analysed on two Varian gas chromatographs; one chromatograph being equipped with two FID detectors and the other with two TCD detectors to determine the concentration of carbonylation reactants and products.

Using the apparatus as described above, a gaseous stream comprising carbon monoxide and hydrogen in a molar ratio of 1:1.8, 9 mol % dimethyl ether, 3.8 mol % nitrogen and 0.2 mol % acetic acid at a gas hourly space velocity of 5000 $h^{-1}$ was introduced into the reactor which was operated at a pressure of 70 barg (7000 kPa), a temperature of 299.5° C. for 212 hours. After 212 hours, the acetic acid supply to the reactor was ceased and replaced by a supply of methanol in an amount of 0.2 mol % (based on the total gaseous feed) and the temperature was increased to 301.5° C. and the reaction was allowed to continue for a period of 146 hours. After 146 hours, the methanol supply to the reactor was ceased and replaced by a supply of water in an amount of 0.1 mol % (based on the total gaseous feed), the amount of nitrogen was increased to 3.9 mol %, the temperature was increased to 312° C. and the reaction was allowed to continue under these conditions for a period of 147 hours. After 147 hours, the methanol supply to the reactor was ceased and replaced by a supply of 0.15 mol % methanol, 0.02 mol % water and 0.01 mol % acetic acid (based on the total gaseous feed), and the amount of nitrogen was decreased to 3.8 mol %, the temperature was increased to 316° C. and the reaction was allowed to continue under these conditions for a further period of 96 hours.

The deactivation rate of the catalyst was determined by the change (° C. loss per day) in the average internal catalyst bed temperature. The average internal catalyst bed temperature was calculated from the sum of the 9 internal thermocouple points divided by 9. The results of this Example are shown in Table 1 below.

TABLE 1

| Hydroxyl compound(s) | Amount of hydroxyl compound(s) (mol %) | Temperature (° C.) | Catalyst deactivation rate (° C. loss per day) |
|---|---|---|---|
| none | 0 | 283.0 | 0.83 |
| acetic acid | 0.2 | 299.5 | 0.01 |
| methanol | 0.2 | 301.5 | 0.00 |
| water | 0.1 | 312.0 | 0.03 |
| acetic acid, methanol and water | 0.18 | 316.0 | 0.04 |

Experiment A

This Experiment demonstrates carbonylation of dimethyl ether with carbon monoxide carried out in the presence of a templated zeolite catalyst and under hydrogen-rich conditions. In this Experiment, neither a hydroxyl compound nor methyl acetate was used as a feed to the carbonylation reaction.

Using the apparatus and 109.9 mL of catalyst as described in Example 1 above, a gaseous carbonylation feed of carbon monoxide and hydrogen in a molar ratio of 1:1.75, and 9 mol % dimethyl ether was supplied to the reactor under reaction conditions of a pressure of 70 barg (7000 kPa), a temperature of 283° C. and a gas hourly space velocity of 5000 $h^{-1}$ and the reaction allowed to continue for a period of 114 hours. The deactivation rate of the catalyst was determined by the change (° C. loss per day) in the average internal catalyst bed temperature and was determined to be 0.83° C. loss per day. The results of this Experiment are shown in Table 1 above.

The invention claimed is:

1. A process for the production of methyl acetate by carbonylation of dimethyl ether which process comprises contacting in a reactor dimethyl ether with carbon monoxide in the presence of a zeolite catalyst, hydrogen, and at least one compound containing a hydroxyl functional group at a temperature of from 250 to 350° C. and at a molar ratio of hydrogen to carbon monoxide of at least 1,
   wherein the process comprises introducing into the reactor the at least one compound containing a hydroxyl functional group, and the process is carried out in the absence of added methyl acetate;
   wherein the at least one compound containing a hydroxyl functional group is one or more hydroxyl compound(s) selected from water, $C_1$-$C_4$ aliphatic alcohols, and $C_1$-$C_4$ aliphatic carboxylic acids; and
   wherein the zeolite is a templated zeolite.

2. A process according to claim 1 wherein the hydroxyl compound(s) is introduced into the reactor in a total amount of up to 1 mol % based on a total gaseous feed to the process including the hydroxyl compound(s), dimethyl ether, carbon monoxide, and hydrogen.

3. A process according to claim 2 wherein the total amount of hydroxyl compound(s) is from 0.01 to 0.5 mol % based on the total gaseous feed to the process.

4. A process according to claim 1, wherein the one or more hydroxyl compound(s) is selected from $C_1$-$C_4$ aliphatic alcohols and $C_1$-$C_4$ aliphatic carboxylic acids.

5. A process according to claim 4 wherein the hydroxyl compound is a $C_1$-$C_4$ aliphatic alcohol.

6. A process according to claim 4 wherein the hydroxyl compound is a $C_1$-$C_4$ aliphatic carboxylic acid.

7. A process according to claim 1 wherein the hydroxyl compound(s) is selected from one or more of acetic acid, methanol and water.

8. A process according to claim 1, wherein the molar ratio of hydrogen to carbon monoxide is in the range 1.5 to 4:1.

9. A process according to claim 1, wherein the catalyst is a zeolite having at least one channel which is defined by an 8-membered ring.

10. A process according to claim 9 wherein the zeolite has a framework type selected from the group consisting of MOR, FER, OFF, CHA, GME, MFS, EON and ETR.

11. A process according to claim 10 wherein the zeolite has the framework type MOR and is mordenite.

12. A process according to claim 1, wherein the process is carried out at a temperature of from 275 to 325° C.

13. A process according to claim 1, wherein methyl acetate product is hydrolysed to acetic acid.

14. A method of maintaining or reducing the deactivation rate of a catalyst in a process for the production of methyl acetate by carbonylation of dimethyl ether which process comprises contacting in a reactor dimethyl ether with carbon monoxide in the presence of a zeolite catalyst, hydrogen, and at least one compound containing a hydroxyl functional group at a temperature of from 250 to 350° C. and at a molar ratio of hydrogen to carbon monoxide of at least 1,
   wherein the process comprises introducing into the reactor the at least one compound containing a hydroxyl functional group and the process is carried out in the absence of added methyl acetate;
   wherein the at least one compound containing a hydroxyl functional group is one or more hydroxyl compound(s) selected from water, $C_1$-$C_4$ aliphatic alcohols, and $C_1$-$C_4$ aliphatic carboxylic acids; and
   wherein the zeolite is a templated zeolite.

15. A process according to claim 1, wherein
   the molar ratio of hydrogen to carbon monoxide is in the range 1 to 12:1;
   the total amount of hydroxyl compound(s) is from 0.01 to 0.5 mol % based on the total gaseous feed to the process; and
   the amount of dimethyl ether is from 1.0 to 20 mol % based on the total gaseous feed to the process.

16. A process according to claim 1, wherein
   the molar ratio of hydrogen to carbon monoxide is in the range 1 to 8:1;
   the total amount of hydroxyl compound(s) is from 0.01 to 0.5 mol % based on the total gaseous feed to the process; and
   the amount of dimethyl ether is from 1.5 to 15 mol % based on the total gaseous feed to the process.

17. A process according to claim 1, wherein
   the molar ratio of hydrogen to carbon monoxide is in the range 1.5 to 4:1;
   the total amount of hydroxyl compound(s) is from 0.01 to 0.5 mol % based on the total gaseous feed to the process; and
   the amount of dimethyl ether is from 1.5 to 15 mol % based on the total gaseous feed to the process.

18. A process according to claim 1, wherein
   the molar ratio of hydrogen to carbon monoxide is in the range 1.5 to 4:1;
   the hydroxyl compound is acetic acid, present in an amount from 0.01 to 0.5 mol % based on the total gaseous feed to the process; and
   the zeolite has a framework type selected from the group consisting of MOR, FER, OFF, CHA, GME, MFS, EON and ETR.

19. A process according to claim 1, wherein
   the molar ratio of hydrogen to carbon monoxide is in the range 1.5 to 4:1;

the hydroxyl compound is methanol, present in an amount from 0.01 to 0.5 mol % based on the total gaseous feed to the process; and the zeolite has a framework type selected from the group consisting of MOR, FER, OFF, CHA, GME, MFS, EON and ETR.

20. A process according to claim 1, wherein the molar ratio of hydrogen to carbon monoxide is in the range 1.5 to 4:1;

the hydroxyl compound is water, present in an amount from 0.01 to 0.5 mol % based on the total gaseous feed to the process; and the zeolite has a framework type selected from the group consisting of MOR, FER, OFF, CHA, GME, MFS, EON and ETR.

* * * * *